United States Patent [19]
Yamamoto et al.

[11] Patent Number: 5,700,256
[45] Date of Patent: Dec. 23, 1997

[54] DISPOSABLE ABSORBENT PAD

[75] Inventors: Masamitsu Yamamoto; Rumi Yamaki, both of Kawanoe, Japan

[73] Assignee: Uni-Charm Corporation, Ehime-ken, Japan

[21] Appl. No.: 676,995

[22] Filed: Jul. 8, 1996

Related U.S. Application Data

[63] Continuation of Ser. No. 321,956, Oct. 12, 1994, abandoned.

[30] Foreign Application Priority Data

Oct. 13, 1993 [JP] Japan .................................. 5-255887

[51] Int. Cl.⁶ .......................... A61F 13/15; A61F 13/20
[52] U.S. Cl. ................... 604/397; 604/385.2; 604/396; 604/402
[58] Field of Search ................ 604/385.1, 385.2, 604/392, 393, 394, 396, 397, 400, 401, 402

[56] References Cited

U.S. PATENT DOCUMENTS

| | | | |
|---|---|---|---|
| 929,166 | 7/1909 | Plamondon | 604/397 |
| 1,103,815 | 7/1914 | Nesgood | 604/401 |
| 1,664,626 | 3/1928 | Ito | 604/400 |
| 1,959,282 | 4/1934 | Bade | 604/401 |
| 2,871,859 | 12/1959 | Dunn | 604/402 |
| 2,977,957 | 4/1961 | Clyne | 604/396 |
| 3,207,158 | 9/1965 | Yoshitake et al. | |
| 3,452,753 | 7/1969 | Sanford . | |
| 4,229,835 | 10/1980 | Shaw | 604/385.2 |
| 4,704,115 | 11/1987 | Buell | 604/385.2 |
| 4,838,886 | 6/1989 | Kent | 604/393 |
| 4,964,860 | 10/1990 | Gipson et al. . | |
| 5,135,522 | 8/1992 | Fahrenkrug et al. | 604/385.2 |
| 5,387,210 | 2/1995 | Murakami | 604/385.1 |

FOREIGN PATENT DOCUMENTS

| | | | |
|---|---|---|---|
| 0450541 | 10/1991 | European Pat. Off. . | |
| 0584823 | 2/1925 | France | 604/401 |
| 57-143502 | 9/1982 | Japan . | |
| 0309712 | 11/1955 | Switzerland | 604/397 |
| 0358765 | 10/1931 | United Kingdom | 604/397 |
| 91/08725 | 6/1991 | WIPO . | |

*Primary Examiner*—John G. Weiss
*Assistant Examiner*—Bruce E. Snow
*Attorney, Agent, or Firm*—Lowe, Price, LeBlanc & Becker

[57] ABSTRACT

An absorbent pad comprising a pad proper adapted to present a boat-shape under the contraction of elastic members contained in respective side flaps, front and rear ends of said pad proper being connected to front and rear ends of an annular elastic waist band by respective pairs of elastic suspending straps.

4 Claims, 2 Drawing Sheets

DISPOSABLE ABSORBENT PAD

This application is a continuation of application Ser. No. 08/321,956 filed Oct. 12, 1994 now abandoned.

BACKGROUND OF THE INVENTION

The present invention relates to so-called disposable absorbent pads, particularly such as incontinence pads, sanitary pads or menstruation pads, adapted to be used only once and then thrown away.

So far as it is known to the inventors, there are several articles of prior art used as incontinence guards which are partially similar in their constructions to a disposable absorbent pad of the present invention. For example, the specification of U.S. Pat. No. 3,452,753 discloses an article comprising a water-impermeable outer cover (not disposable) designed for elastic fitness around the wearer's waist- and leg-openings and a support attached to the inner side of the cover for a separate absorbent pad and Japanese Patent Application Disclosure Gazette No. 1982-143502 discloses an article comprising an elastically stretchable waist band and straps interconnected so as to form a supporter (not disposable) to support a separate absorbent pad, wherein the supporter surrounds the wearer's legs not completely but partially.

These well known techniques are similar to the invention in that there are provided straps connected to an elastically stretchable waist band to support an absorbent pad in direct or indirect manner and a basic body or supporter is configured so as to surround the wearer's legs not completely but partially.

There are well known many other incontinence guard articles, for example, a disposable incontinence guard article comprising a liquid-permeable topsheet, a liquid-impermeable backsheet, a liquid-absorbent core sandwiched between these two sheets, and elastically stretcheable members arranged along waist- and leg-openings and such an article further comprising a separate absorbent pad to be attached to the inner side of the article.

Straps employed by the prior art disclosed in U.S. Pat. No. 3,452,753 appears to be provided for the purpose of assuring a stability with which a pad proper of the article can be put on wearer's body and the strap employed by the prior art disclosed in Japanese Patent Application Disclosure Gazette No. 1982-143502 functions only as a component of the supporter.

These straps have no elastic stretchability and therefore no function for pulling the basic body or supporter up toward the wearer's crotch. Accordingly, the absorbent pad is not maintained in sufficiently close contact with the wearer's crotch to prevent the leakage of excretion from occurring around this zone.

SUMMARY OF THE INVENTION

In view of the problem as has been mentioned above, it is a principal object of the invention to maintain a pad proper in close contact with the wearer's crotch by elastically suspending the pad proper.

To achieve the object set forth above, the present invention broadly resides in an improved absorbent pad of disposable type comprising a pad proper, an annular elastic waist band and elastic suspending straps. Said pad proper comprises a liquid-permeable topsheet, a liquid-impermeable backsheet and an absorbent core sandwiched between these two sheets, wherein side flaps extend outward from laterally opposite side edges of said core, said side flaps are provided at least adjacent their outer side edges with elastic members being stretchable longitudinally of said outer side edges, said side flaps are folded inward, respectively, and longitudinally opposite ends of said side flaps thus folded inward are fixed, in their longitudinally stretched states, to said pad proper, and wherein a longitudinally front end of said pad proper is connected to a front side of said waist band and a longitudinally rear end of said pad proper is connected to a rear side of said waist band by respective pairs of said suspending straps spaced from each other.

Preferably, sleeves are formed by the respective outer side edges of said side flaps and said elastic members are received by said sleeves, respectively, so that said elastic members extend beyond longitudinally opposite ends of the respective sleeves and these extensions define said suspending straps. Preferably, each pair of straps is connected to said waist band at two positions further spaced from each other than two positions at which this pair of straps is connected to one of longitudinally opposite ends of said pad proper. Preferably, said side flaps are formed by at least portions of said top- and backsheets extending from the laterally opposite side edges of said core.

The pad according to the invention may be used independently or with a separately provided outer cover, if it is desired. In actual use of the pad, as the annular elastic waist band is placed at a predetermined location around the wearer's waist, the pad proper is pulled up against the wearer's crotch by the contraction of the elastic suspending straps and simultaneously the outer side edges of the respective side flaps are brought under the effect of the elastic members contained in these outer side edges into close contact with the wearer's crotch, particularly, respective groins. When it is desired that the pad proper should be more correctly positioned against the wearer's crotch, the pad proper may be held by the hand, then pulled down against the action of the elastic suspending straps and released. Thereupon, the pad proper will be automatically brought back against the wearer's crotch by the contraction of the elastic suspending straps. Obviously, such operation may be repeated, if necessary.

With the pad proper correctly placed on the wearer's body in this manner, the side flaps are risen by the contraction of the elastic members contained in the outer side edges thereof against the wearer's skin, thus generally presenting a boat-shape having a substantially U-shaped cross-section and a substantially bow-shaped longitudinal section, so that the side flaps may completely receive and guide liquid excretion to the core where excretion is absorbed and held.

BRIEF DESCRIPTION OF THE DRAWINGS

The invention will be described in more detail by way of example in reference with the accompanying drawings, in which.

PREFERRED EMBODIMENTS OF THE INVENTION

Figure 1:
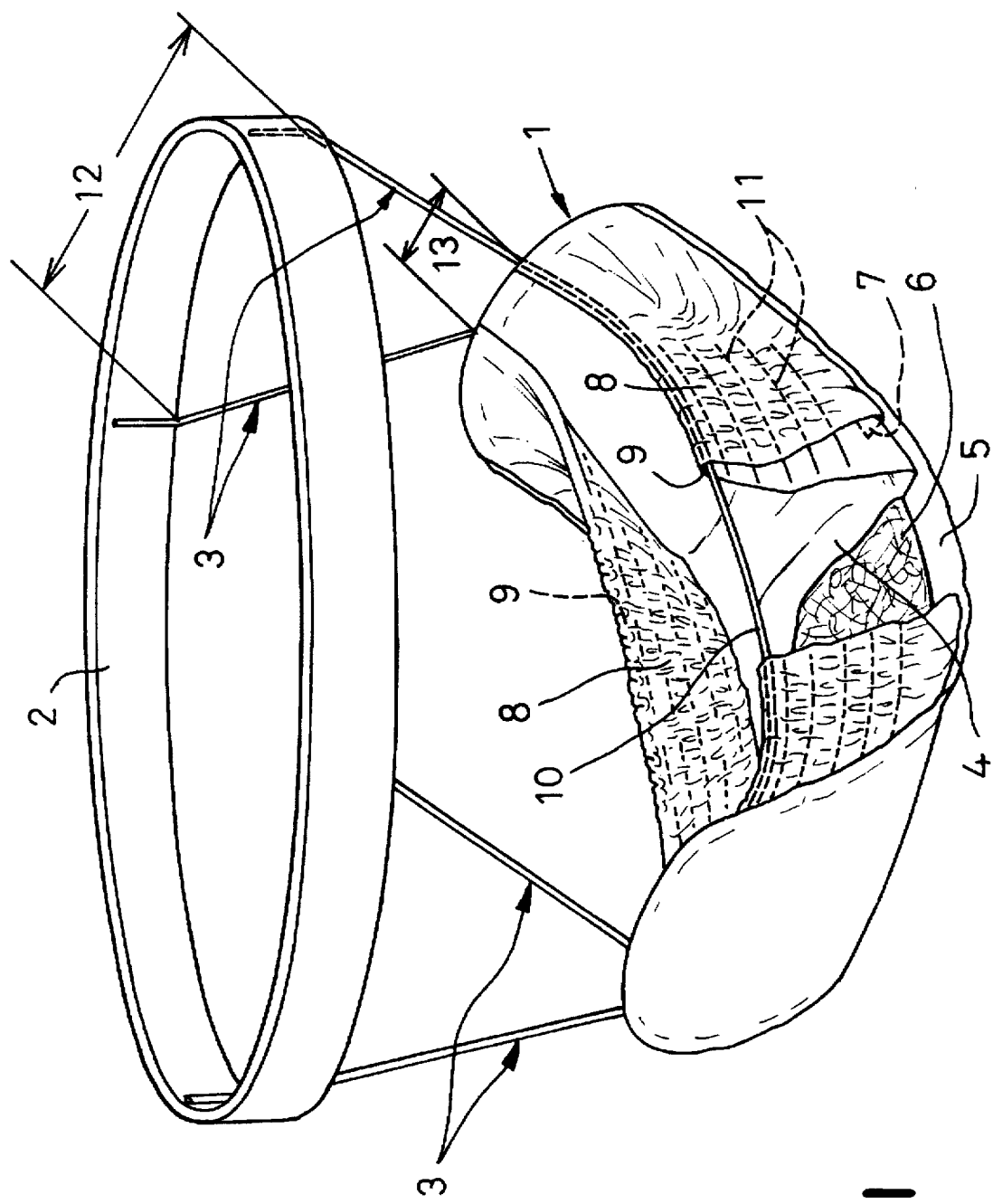
FIG. 1 is a partially broken-away perspective view showing an embodiment of an incontinence pad constructed according to the invention as developed for actual use.

Referring to FIG. 1, a pad of the invention generally comprises a pad proper 1, an annular elastic waist band 2 and elastic suspending straps 3.

The pad proper 1 comprises a liquid-permeable topsheet 4, a liquid-impermeable backsheet 5, a relatively short and narrow liquid-absorbent core 6 sandwiched between these two sheets 4, 5 and side flaps 8 comprising respective portions of the topsheet 4 extending outward from laterally opposite side edges of the core 6 and folded back so that laterally opposite side edges 7 of these folded portions may be bonded to laterally opposite side edges of the backsheet 5 by suitable bonding means such as ultrasonic welding or adhesive. Portions of the top- and backsheets 4, 5 extending from longitudinally opposite ends of the core 6 are also bonded together by the similar bonding means. When the pad proper 1 is for incontinence guard, it may be dimensioned so as to cover urinary organs and a peripheral region therearound or may be slightly larger than the average size of sanitary ordinary menstruation pads for visual impression. It should be understood that the pad proper 1 may be dimensioned to cover anus and its periphery as well, if necessary.

As will be apparent to those skilled in the art without illustration, it is also possible to form the side flaps 8 from portions of both the topsheet 4 and the backsheet 5 extending from the laterally opposite side edges of the core 6 and folded back together in the same manner as the topsheet 4 alone has been folded in the above-mentioned arrangement or from portions of the backsheet 5 instead of the topsheet 4 extending from the laterally opposite side edges of the core and folded back in the same manner. In these alternative arrangements, the side flaps 8 will be liquid-impermeable. As will be apparent to those skilled in the art without illustration, it is also possible to form liquid-permeable or liquid-impermeable side flaps 8 from suitable sheets provided separately of both the top- and backsheets 4, 5 and, in such alternative arrangement, these separate sheets will be bonded to the portions of the top- and backsheets 4, 5 slightly extending outward from the laterally opposite side edges of the core 6.

Sleeves 9 are defined by the respective side flaps 8 along the respective folding lines to receive elastic members 10 extending therethrough. Between the folded and nonfolded portions of the respective side flaps 8, a plurality of longitudinally stretchable elastic members 11 are adhesively interposed in their stretched states so that these elastic members 11 are transversely spaced one from another in parallel from the respective side edges 7 of the folded portions to the associated sleeves 9. The side flaps 8 arranged as has been described are now folded back toward the portion of the topsheet 4 defining the top of the core 6 and longitudinally opposite ends thereof are bonded, in their longitudinally stretched states, to said portion of the topsheet 4 by said suitable bonding means.

The pad proper 1 of the foregoing arrangement has the side flaps 8 risen by the contraction of the elastic members operatively associated therewith against the wearer's skin, generally presenting a boat-shape having a substantially U-shaped cross-section and a substantially bow-shaped longitudinal section.

The respective suspending straps 3 are defined by portions of the respective elastic members 10 extending beyond longitudinally opposite ends of the respective sleeves 9. Consequently, the respective suspending straps 3 elastically act integrally with the associated ones of elastic members 10. The respective suspending straps 3, i.e., the respective elastic members 10 have a stretching stress selected so as to prevent the waist band 2 put around the wearer's waist from slipping down. Obviously, the respective suspending straps 3 may comprise elastic members provided separately of the respective elastic members 10 and may be bonded to the associated elastic members 10 or longitudinally opposite ends of said folded portions of the respective side flaps 8.

The waist band 2 has a considerably larger width and a higher stretching stress with respect to the respective suspending straps 3. The respective suspending straps 3 have their ends connected to front and rear sides of the waist band 2 at locations circumferentially spaced one from another. Each pair of adjacent suspending straps 3 are larger spaced (12) from each other along the waist band 2 than they are spaced (13) from each other along the front or rear end of the core 6 in order that the pad proper 1 can be stably suspended.

Figure 2:
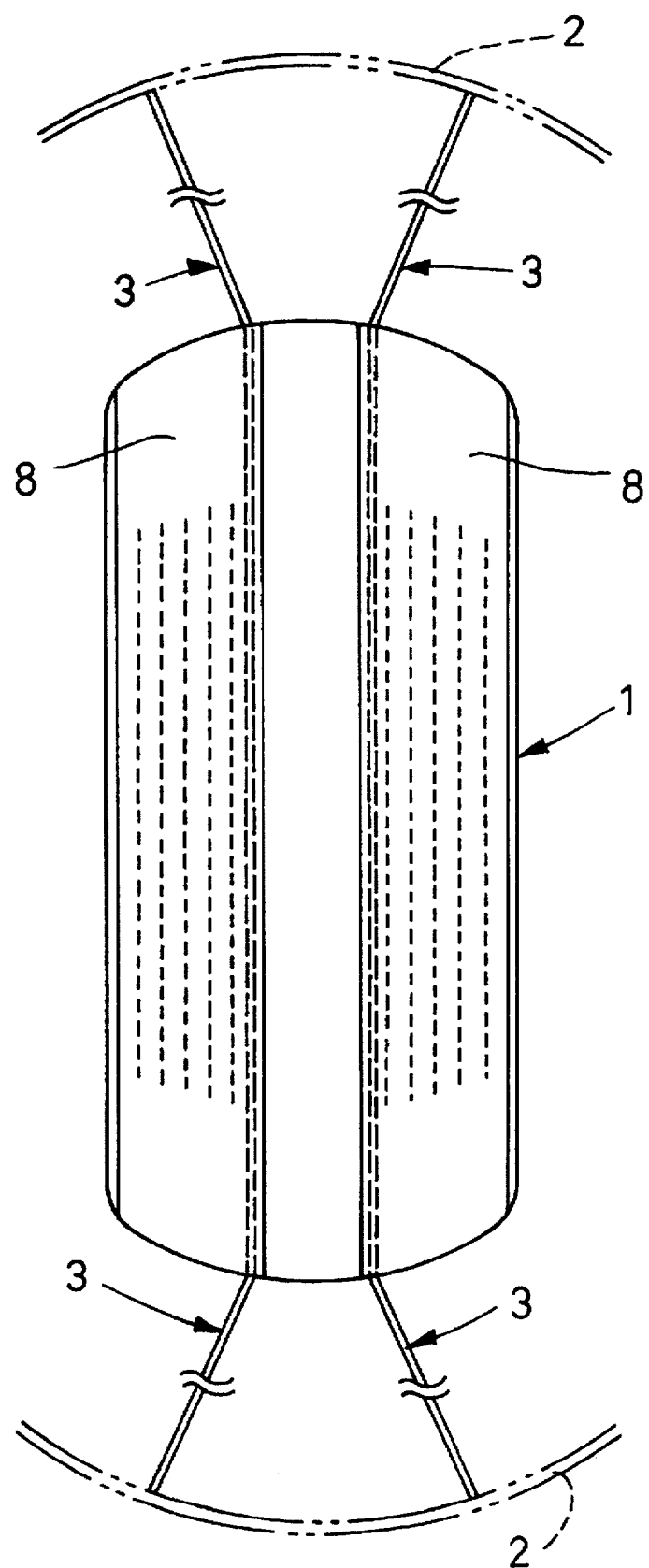
FIG. 2 is a plan view showing this pad as collapsed for storage.

Referring to FIG. 2, the respective side flaps 8 inwardly collapsed in flat states as the pad proper 1 is subjected to a tension exerted thereon in the longitudinal direction. The pad proper 1 thus flattened may be longitudinally folded to be compactly packaged.

The pad proper 1 may be made of the same materials as usually used for disposable diapers, sanitary napkins or menstruation pads and the like. For example, the topsheet 4 may be made of a nonwoven fabric, the backsheet 5 may be made of a plastic film and the core 6 may be made of fluff pulps mixed with high absorption polymer powders. The waist band 2 and the suspending straps 3 may comprise conventional cords, belts or the like having a rubber elasticity.

What is claimed is:

1. A disposable absorbent pad comprising a pad, an annular elastic waist band and two pairs of elastic suspending straps bonded to said waist band, said pad comprising a liquid-permeable topsheet, a liquid-impermeable backsheet and an absorbent core sandwiched between said topsheet and said backsheet, wherein side flaps extend outward from laterally opposite side edges of said core, said side flaps having sleeves at their outer side edges, said sleeves each containing elastic members being longitudinally stretchable, said elastic members extending beyond longitudinally opposite ends of the respective sleeves and these elastic members further defining said pairs of suspending straps, said side flaps are folded inward, and longitudinally opposite ends of said side flaps thus folded inward are fixed to said pad, and wherein a longitudinally front end of said pad is connected to a front side of said waist band by one of said two pairs of suspending straps and a longitudinally rear end of said pad is connected to a rear side of said waist band by the other of said two pairs of suspending straps.

2. A disposable absorbent pad according to claim 1, wherein each pair of strap is connected to said waist band at two positions further spaced from each other than two positions at which this pair of straps is connected to one of longitudinally opposite ends of said pad.

3. A disposable absorbent pad according to claim 1, wherein said side flaps are formed by at least portions of said topsheet and said backsheet extending from the laterally opposite side edges of said core.

4. A disposable absorbent pad according to claim 1, wherein said pad is adapted to present a boat-shape under the contraction of the elastic members of said side flaps.

* * * * *